(12) United States Patent
Brumbaugh et al.

(10) Patent No.: US 8,389,026 B2
(45) Date of Patent: Mar. 5, 2013

(54) COMPOSITION AND METHOD FOR SKIN REPAIR

(75) Inventors: Ernest H. Brumbaugh, Rockford, MI (US); Arun Rajgopal, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 226 days.

(21) Appl. No.: 12/872,311

(22) Filed: Aug. 31, 2010

(65) Prior Publication Data

US 2011/0052741 A1  Mar. 3, 2011

Related U.S. Application Data

(60) Provisional application No. 61/239,240, filed on Sep. 2, 2009.

(51) Int. Cl.
*A61K 36/00* (2006.01)
*A61K 31/74* (2006.01)

(52) U.S. Cl. ............... 424/725; 424/78.02; 424/774; 424/769

(58) Field of Classification Search .............. None
See application file for complete search history.

(56) References Cited

U.S. PATENT DOCUMENTS

| | | | |
|---|---|---|---|
| 5,616,323 A | 4/1997 | Ginoux et al. | |
| 5,747,043 A | 5/1998 | Ginoux et al. | |
| 6,084,152 A | 7/2000 | Kwak et al. | |
| 6,958,164 B2 | 10/2005 | Dutta-Roy | |
| 7,132,118 B2 | 11/2006 | Dreyer et al. | |
| 7,150,870 B2 | 12/2006 | Okada et al. | |
| 7,468,195 B2 | 12/2008 | Diehl | |
| 2002/0182269 A1 | 12/2002 | Dreyer et al. | |
| 2003/0180231 A1 | 9/2003 | Danoux et al. | |
| 2003/0203052 A1 | 10/2003 | Dreyer et al. | |
| 2005/0025737 A1* | 2/2005 | Sebagh | 424/74 |
| 2006/0286188 A1 | 12/2006 | Mower et al. | |
| 2007/0202206 A1 | 8/2007 | Palu et al. | |
| 2007/0218045 A1 | 9/2007 | Diehl | |
| 2007/0237735 A1 | 10/2007 | Denommee | |
| 2008/0199489 A1 | 8/2008 | Parrinello | |
| 2008/0248138 A1* | 10/2008 | Greco | 424/725 |
| 2009/0092591 A1 | 4/2009 | Diehl | |

FOREIGN PATENT DOCUMENTS

| | | |
|---|---|---|
| CN | 101 129 946 | 2/2008 |
| CN | 101 497 851 | 8/2009 |
| EP | 1 607 098 | 12/2005 |
| EP | 1607098 A1 * | 12/2005 |
| FR | 2 786 778 | 6/2000 |
| WO | WO 2005/046574 | 5/2005 |
| WO | WO 2006/030111 | 3/2006 |
| WO | WO 2007/000619 | 1/2007 |
| WO | WO 2008/073194 | 6/2008 |

OTHER PUBLICATIONS

International Preliminary Report on Patentability for PCT/US2010/046613, dated Mar. 6, 2012, 5 pages.
Holdsworth, D. K. et al., "Medicinal and Poisonous Plants from Manus Island", *Science in New Guinea*, vol. 1, No. 3-4, Jan. 1, 1973, pp. 11-16.
Information Sheet for "Citrifoline", C.E.P, Sep. 30, 2005, 2 pages.
Article entitled, "Extramel® Microgranules-Antioxidant Melon Extract", *Seppic-Subsidiary of the Air Liquide Group*, Sep. 2005, 2 pages.
Sang et al., "Flavonol Glycosides and Novel Iridoid Glycoside from the Leaves of *Morinda citrifolia*", *J. Agric. Food Chem.*, vol. 49, No. 9, 2001, pp. 4478-4481.

* cited by examiner

*Primary Examiner* — Chris R Tate
*Assistant Examiner* — Deborah Davis
(74) *Attorney, Agent, or Firm* — Brinks Hofer Gilson & Lione; G. Peter Nichols

(57) ABSTRACT

A composition and a method of using the composition is described that is effective to protect or repair oxidative damage to DNA in mammalian skin by up regulating each of SIRT1, Gadd45b, and SOD2. The composition includes at least two of a candle bush extract, noni leaf extract, and melon extract with each present in an amount such that the composition is effective to up regulate each of SIRT1, Gadd45b, and SOD2.

10 Claims, 1 Drawing Sheet

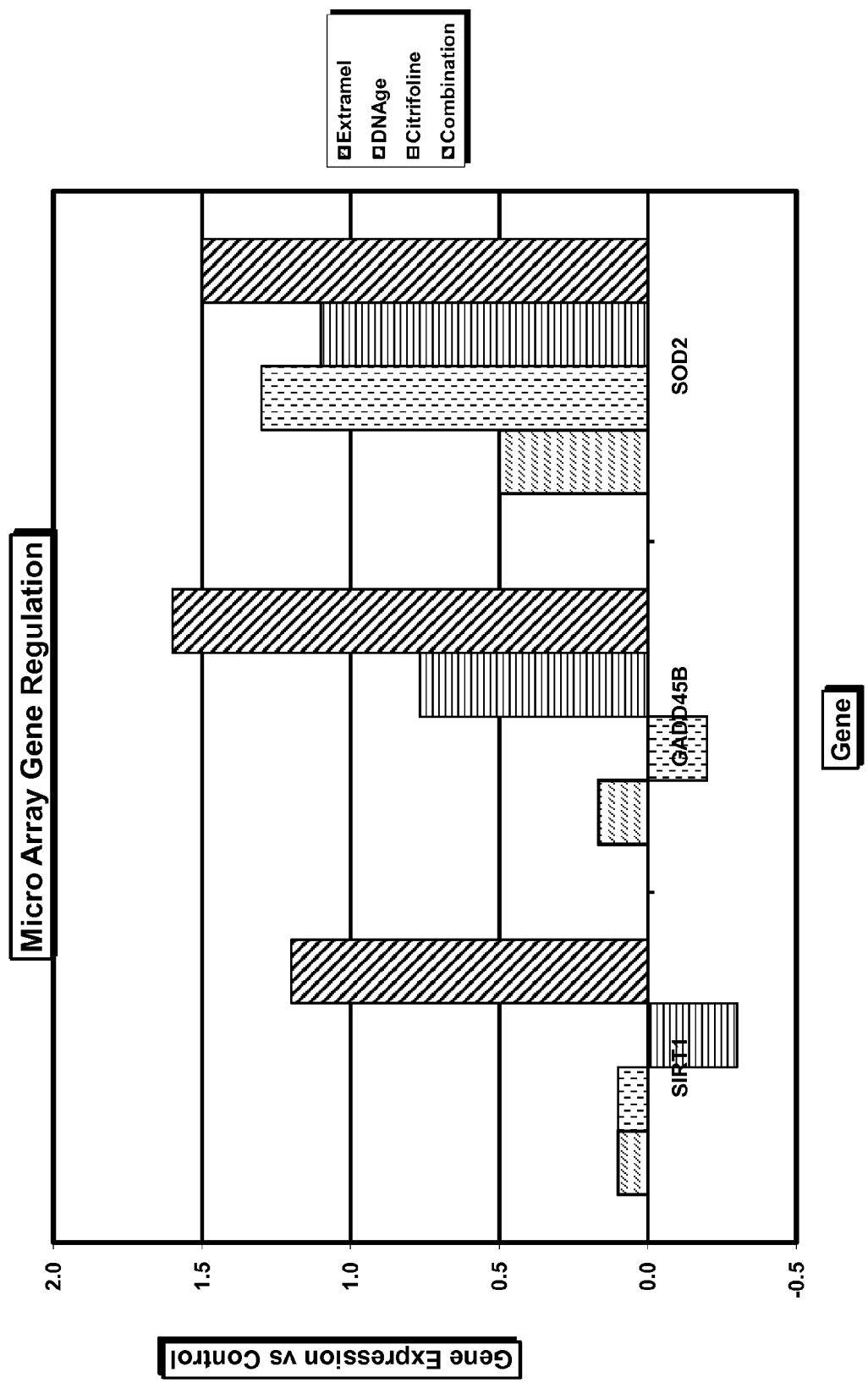

US 8,389,026 B2

COMPOSITION AND METHOD FOR SKIN REPAIR

This application claims priority to U.S. Application Ser. No. 61/239,240 filed Sep. 2, 2009, the entire contents of which are incorporated herein by reference.

The present invention relates to a composition containing at least two plant extracts and, in certain embodiments, containing three plant extracts that individually and/or collectively are present in amounts effective to increase the protective and/or reparative cellular, mitochondrial, and extracellular DNA genetic responses to oxidative stress. The composition of the present invention, which includes a combination of plant extracts, up regulates each of SIRT1, GADD45B, and SOD2 in a synergistic manner. In certain embodiments, the composition is formulated as a cosmetic or dermatological preparation.

Skin ages in response to various agents that cause stress, such as oxidative stress due to the several Reactive Oxygen Species (ROS). ROS can be the result of metabolic processes, but can also be caused by persistent low level UV radiation that generates ROS that can cause DNA damage. As a result of such DNA damage, the skin is less able to renew itself, the effects of which are often visible and unwanted.

Cosmetic and dermatological formulations have been developed in an effort to address the causes of ROS. Some formulations seek to protect the skin from the oxidative stress. Others seek to eliminate or reduce the ROS once formed within the skin. For example, sunscreens are incorporated into cosmetics in an effort to reduce the amount of UV radiation entering the skin. Although sunscreens are effective, they do not protect against all forms of UV radiation. Also, sunscreens unfortunately inhibit production of vitamin D. In addition, cosmetic formulations containing sunscreen compositions often wash off from sweat or water and are often greasy or oily, which contributes to a sense of dissatisfaction.

Alternatively, antioxidants are incorporated into cosmetics in an effort to react with or neutralize the generated ROS. Products that contain antioxidants or other ingredients to counteract ROS are generally only active when they are in contact with the ROS. As a result, the ROS that is present in the skin is causing damage until such time as the antioxidant or counteractant comes into contact with the ROS.

Another approach is to incorporate moisturizers and emollients in an effort to reduce moisture loss from damaged skin and to add suppleness to dry or thin skin. While incorporating emollients and moisturizers into cosmetic formulations will reduce transepidermal water loss from skin, their presence does not change the condition of the damaged skin.

While each of the above the above approaches has merit, the present inventors have found that by up regulating certain DNA repair enzymes, the damage caused by ROS can be repaired and the DNA can be protected from damage (or further damage) that can be caused by ROS. For example, SIRT1 has been implicated in cell longevity and DNA repair. In addition, Gadd45b (growth arrest and DNA damage) is a multifunctional protein that has been shown to modulate the activity and accessibility of certain repair enzymes. Likewise, the SOD2 gene has been implicated in mitochondrial DNA protection.

Each of these genes helps to protect or repair DNA, which should reduce permanent skin damage and should allow the repair process of the skin to proceed. Surprisingly, the present inventors found that the composition according to the present invention synergistically up regulates each of SIRT1, Gadd45b, and SOD2 genes.

SUMMARY

The present invention provides a composition containing at least two extracts selected from candle bush extract (*cassia alata*), noni leaf extract (*morinda citrifolia*), and melon extract (*cucumis melo*) such that each extract included in the composition is present in an amount such that the composition is effective to up regulate each of SIRT1, Gadd45b, and SOD2. In an embodiment, the composition contains each of candle bush extract (*cassia alata*), noni leaf extract (*morinda citrifolia*), and melon extract (*cucumis melo*) such that each extract included in the composition is present in an amount such that the composition is effective to up regulate each of SIRT1, Gadd45b, and SOD2.

Another aspect of the invention relates to a method of protecting or repairing oxidative damage comprising administering a composition comprising at least two of a candle bush extract (*cassia alata*), noni leaf extract (*morinda citrifolia*), and melon extract (*cucumis melo*) such that each extract included in the composition is present in an amount such that the composition is effective to up regulate each of SIRT1, Gadd45b, and SOD2. The method also includes topically applying the above compositions to the skin of a mammal in an amount effective to up regulate each of SIRT1, Gadd45b, and SOD2.

As used herein, "safe and effective amount" means a sufficient amount of a compound, composition or other material described by this phrase to significantly induce a positive modification in the condition being treated, but low enough to avoid undue side effects (e.g., significant skin irritation or sensitization), within the scope of sound judgment of the skilled person. The safe and effective amount of the compound, composition or other material may vary with the particular skin being treated, the age and physical condition of the biological subject being treated, the severity of the condition, the duration of treatment, the nature of concurrent therapy, the specific compound, composition, or other material employed, the particular cosmetically acceptable topical carrier utilized, and the factors within the knowledge and expertise of the skilled person.

Unless otherwise specified, all recited percentages are by weight.

As used in the specification and claims, the terms "candle bush extract" and "*Cassia alata*" are used synonymously and refer to the extracts obtained from the plants identified as *Cassia alata* from the plant family Fabaceae as well as to those plants having related names as noted below. As used in the specification and claims, the terms "noni leaf extract" and "*Morinda citrofolia*" are used synonymously and refer to the extracts obtained from the plants identified as *Morinda citrofolia* which is from the genus *Morinda* L. as well as to related plants referred to below. The terms "melon extract" and "*cucumis melo*" are used synonymously and refer to extracts obtained from the plants identified as *cucumis melo*, which is from the genus *Cucumis* L as well as to related plants and identified below.

BRIEF DESCRIPTION OF THE DRAWING

FIG. 1 shows the regulation of the genes SIRT1, GADD45B, and SOD2 by (1) a composition containing only 0.3% DN-AGE LS 9653 (containing from about 0.5% to about 1.5% of candle bush extract), (2) a composition containing only 0.1% CITROFOLINE (containing from about 1.5% to about 3.5% of noni leaf extract), (3) a composition containing only 0.5% of EXTRAMEL C (containing about 20% of melon extract), and (4) a composition containing 0.3% DN-AGE LS 9653, 0.1% CITROFOLINE, and 0.5% of EXTRAMEL C.

DETAILED DESCRIPTION

In accordance with an aspect of the present invention a composition is provided that contains at least two plant extracts selected from candle bush extract (*cassia alata*), noni leaf extract (*morinda citrifolia*), and melon extract (*cucumis melo*) such that each extract included in the composition is present in an amount such that the composition is effective to up regulate each of SIRT1, Gadd45b, and SOD2.

Candle Bush Extract

Candle bush extract is a common name for the plant species *cassia alata*. Other related specie names may include *Senna alata* (L.) Roxb., *Cassia alata* L., *Cassia alata* L. var. *perennis* Pamp., *Cassia alata* L. var. *rumphiana* DC., *Cassia bracteata* L. f., *Cassia herpetica* Jacq., *Cassia rumphiana* (DC.) Bojer, *Herpetica alata* (L.) Raf. Other related common names may include Dadmurdan (Hi), Guajavo, Datkapat (Hi), Quatre Epingles, Dartres, Dartrier, Carrion Crow Bush, Candlebush, Cattiping, emperor's candlesticks, Katepin, Epis d'Or, Candlesticks, Guacamaya Francesa, Mocote, Flor del Secreto, Candlestick Plant, Casse de Java, Mulamula, Catépen, Golden Candelabra Tree, Candle Bush, Candelabra Bush, Roman Candle Tree, Herbe à Dartres, Fleur St. Christophe, Ringworm Bush, Ringworm *Cassia* (En), Ringworm Plant, Ringworm Shrub (En), Acapulco, Fleur à Dartre, Senamukhi (Hi), Seven Golden Candlesticks, Taperibá Guazú, Taratana, Sorontocontil, Talentro, Tulipán, Vilayati-aghatea (Hi), Winged *Senna* (En), Zerbe St. Christophe. Unless otherwise noted, a reference to *cassia alata* is meant to include each of the related specie names set forth above. For example, a reference to *cassia alata* includes *Senna alata* (L.) Roxb.

*Cassia alata* is obtained from plants of the family Fabaceae. The extract may be obtained by known methods of extracting plants or parts thereof. For example, processes such as maceration, remaceration, digestion, agitation maceration, vortex extraction, ultrasonic extraction, countercurrent extraction, percolation, repercolation, evacolation (extraction under reduced pressure), diacolation and solid/liquid extraction under continuous reflux in a Soxhlet extractor, are familiar to the expert and may be used. Further details of such can be found in Hagers Handbuch der pharmazeutischen Praxis (5th Edition, Vol. 2, pp. 1026-1030, Springer Verlag, Berlin-Heidelberg-New York 1991), the contents of which are incorporated herein by reference.

Fresh or dried plants or parts thereof are suitable as the starting material although plants and/or plant parts which may be mechanically size-reduced and optionally defatted before extraction are normally used. Any size reduction method may be used. For example, comminution with a bladed tool may be used. The leaves of the plant are suitable for extraction.

Typical solvents for the extraction process are organic solvents, water or mixtures of organic solvents and water. For example, low molecular weight alcohols, esters, ethers, ketones or halogenated hydrocarbons with more or less large water contents (distilled or non-distilled), preferably aqueous alcoholic solutions with more or less large water contents can be used. Extraction with water, methanol, ethanol, propanol, butanol and isomers thereof, acetone, propylene glycols, polyethylene glycols, ethyl acetate, dichloromethane, trichloromethane and mixtures thereof are suitable.

The extraction process is generally carried out at a temperature of about 20° to about 100° C., or in a range of about 80° to about 100° C., or in a range from about 80° to 90° C. In one possible embodiment, the extraction process may be carried out in an inert gas atmosphere to avoid oxidation of the ingredients of the extract. The extraction times are selected and may depend upon the starting material, the extraction process, the extraction temperature and the ratio of solvent to raw material, etc. After the extraction process, the crude extracts obtained may optionally be subjected to other typical steps, such as for example purification, concentration and/or decoloration. If desired, the extracts thus prepared may be subjected, for example, to the selective removal of individual unwanted ingredients. The extraction process may be carried out to any degree, but is usually continued to exhaustion. Typical yields (=extract dry matter, based on the quantity of raw material used) in the extraction of dried plants or dried plant parts (optionally defatted) are in the range from 10 to 20, preferably 12 to 19 and more particularly 13 to 16% by weight.

The extracts of the plant *Cassia alata* according to the invention generally contain substances from the group consisting of flavone derivatives, more particularly kaempferol and kaempferol derivatives, tannins, coumarins, anthraquinones and also free phenol acids, more particularly p-hydroxybenzoic acid.

Flavone derivatives in the context of the invention are understood to be those that can be isolated from the plant *Cassia alata*. More particularly, they are hydrogenation, oxidation or substitution products of 2-phenyl-4H-1-benzopyran; hydrogenation may already be present in the 2,3-position of the carbon chain, oxidation may already be present in the 4-position and substitution products are understood to be the replacement of one or more hydrogen atoms by hydroxy or methoxy groups. Accordingly, this definition also encompasses flavans, flavan-3-ols (catechols), flavan-3,4-diols (leucoanthocyanidines), flavones, flavonols and flavonones in the traditional sense. Noted flavone derivatives isolated from the plant *Cassia alata* are kaempferol and kaempferol such as, for example, kaempferol-3-O-sophoroside, kaempferol-7-rhamnoside, kaempferol-3,7-dirhamnoside.

Tannins in the context of the invention are tannins that can be isolated from the plant *Cassia alata*. More particularly, they are polyphenols that may also be referred to as gallotannins by virtue of their derivation from gallic acid. Tannins are also substances formed by oxidative coupling of the galloyl residues in 1,2,3,4,6-pentagalloyl-D-glucose and derivatives of such substances.

Coumarins are understood to be coumarins that can be isolated from the plant *Cassia alata*. The name coumarin is a synonym and is equivalent to the names coumarin, chromen-2-one, 2H-1-benzopyran-2-one, o-coumaric acid lactone and tonka bean camphor. Coumarin is the cyclization product from coumaric acid. Coumaric acid is ortho-hydroxycinnamic acid. In the context of the invention, coumarin is also understood to include the glucoside of coumaric acid.

Anthraquinones are anthraquinones that can be isolated from the plant *Cassia alata*. More particularly, they are anthraquinone or oxidation or substitution products of 9,10-anthracene dione, substitution products being understood to be the replacement of one or more hydrogen atoms by hydroxy or methyl groups. The anthraquinones may be alizarin, quinizarin, chrysazin, hytsazarin, purpurin, chrysophanic acid, quinalizarin and flavopurpurin.

Free phenol acids are understood to be those that can be isolated from the plant *Cassia alata*, preferably p-hydroxybenzoic acid and o-hydroxybenzoic acid or salicylic acid.

Further details of extracts of *cassia alata* can be found in US 2003/0180231, the contents of which are incorporated herein by reference.

A commercial product containing an extract of *Cassia alata* is available from Laboratories Serobiologiques as DN-AGE LS 9653 (which identifies the extract as *senna alata* (L.) Roxb. This product contains water, glycerin and *cassia alata* leaf extract and is soluble in water and insoluble in fats and oils. The *cassia alata* leaf extract is present in this product in an amount from about 0.5% to about 1.5%.

In one aspect of the present invention the candle bush extract is present in an amount in the range from about 0.01% to about 1% of the composition and can be present in an amount in the range from about 0.05% to about 0.5%. In another aspect, the candle bush extract is present in an amount in the range from about 0.1% to about 0.3% of the composition.

Noni Tree Extract

The noni tree extract is a common name for *Morinda citrofolia* which is from the genus *Morinda* L. Accordingly, the noni tree extract useful in the present invention may be selected from the plant species obtained from the genus *Morinda* L.

The noni tree extract may be obtained from the leaves although it is contemplated that the extract may be derived from other parts of the plant. In some embodiments, an extract may be obtained using the following process. First, relatively dry leaves from the *Morinda citrifolia* L. plant are collected, cut into small pieces, and placed into a crushing device such as a hydraulic press where the leaf pieces are crushed. In some embodiments, the crushed leaf pieces may then be percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove substantially all the liquid. The resulting dry leaf extract may be referred to as the "primary leaf extract."

In some embodiments of the present invention, the primary leaf extract is pasteurized to at least partially sterilize the extract and destroy objectionable organisms. The primary leaf extract is pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

The primary leaf extract, whether pasteurized and/or purified, may then be further fractionated into two individual fractions: a dry hexane fraction, and an aqueous methanol fraction. This can be accomplished using a gas chromatograph containing silicon dioxide and $CH_2Cl_2$-MeOH ingredients and using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined.

A suitable commercial product can be obtained from CEP under the tradename CITRIFOLINE and it contains from about 1.5% to about 3.5% of the dry extract in butylene glycol and water. The dry extract is obtained by hydroglycolic extraction from the leaves of *Morinda citrifolia* that has been titrated in citric acid. The commercial product is soluble in water and in propylene glycol and insoluble in vegetable and mineral oils.

The noni extract may be present in amounts ranging from about 0.01% to about 1% and may be present in amounts ranging from about 0.03% to about 0.5%. In one aspect, the noni extract may be present in an amount ranging from about 0.05% to about 0.25%.

Melon Extract

Natural melon or *cucumis melo* contains a mixture of ingredients that are beneficial to the skin including superoxide dismutase (SOD), catalase, vitamins, coenzyme Q10, lipoic acid, glutathione, and mineral salts such as potassium, magnesium, calcium, and selenium. Various antioxidants such as, but not limited to, SOD and catalase minimize free radical damage to the skin, thereby reducing or slowing down the signs of aging.

In one embodiment, the melon extract is obtained from a *cucumis melo* variety. In another embodiment, the melon extract is obtained from a *cucumis melo* obtained by genetic crossing, such as the 95LS444 line, or one of the hybrids obtained from this line (see U.S. Pat. Nos. 5,747,043 and 5,616,323, both of which are hereby incorporated by reference). This melon variety has a typical shelf life on the order of 14 days, which is approximately three times more than the usual variety. The presence of antioxidants, especially SOD and catalase, explains in part the exceptionally long storage life of these unique melon varieties.

The melon extract can be produced using only the melon pulp without any solvent. In another embodiment, the desired melon extract may be obtained by pressing or grinding in an aqueous medium at a pH in the range between about 5 to about 9, typically about 7.5, followed by recovery of the supernatant by, for example, centrifugation or filtration. The recovered supernatant may be used as is or may be dried into microgranules. The drying may be accomplished by freeze drying or other known methods.

The microgranules of the melon extract may be used in the formulation as is, may be incorporated into nanospheres, may be encapsulated in a substance such as a hydrogenated fat or encapsulated in a micro or macro emulsion. Additionally, the raw melon extract may be coated into microgranules with vegetable fats. The microgranules may comprise, for example, about 50% extract and about 50% fat, and may be easily incorporated in cosmetic formulations. As those skilled in the art will appreciate, the percentages of the extract and fat may be varied according to a desired composition by combining the extract with a vegetable fat. A strong barrier for antioxidants and bioavailability is produced that also protects and stabilizes the antioxidants against moisture, temperature, acidic pH, etc. A description of one such coated melon extract is provided in US 2005/0025737, which is incorporated herein by reference.

Alternatively, the extract may be encapsulated using a hydroxypropyltrimonium maltodextrin crosspolymer or similar substance. A description of one such encapsulated melon extract is provided in U.S. Pat. No. 7,132,118, which is incorporated herein by reference. A suitable commercial product is EXTRAMEL™ C from Bionov. This product contains about 20% melon extract and about 80% of the hydroxypropyltrimonium maltodextrin crosspolymer.

The melon extract obtained by any of the above suitable methods is typically standardized with respect to superoxide dismutase (SOD) activity per mg of proteins. In certain embodiments of the present invention the melon extract provides SOD activity of at least 6 units per mg of proteins and may provide SOD activity of at least 14 units per mg of proteins, or an SOD activity of at least 18 units per mg of proteins. In further embodiments, the melon extract provides an SOD activity in a range from about 20 to about 100 units per mg of proteins, and may provide an SOD activity in a range from about 30 to about 50 units per mg of proteins.

The melon extract may be present in amounts ranging from about 0.01% to about 3% and may be present in amounts ranging from about 0.03% to about 2%. In one aspect, the melon extract may be present in amounts ranging from about 0.05% to about 1%.

The compositions of the present invention include candle bush extract, noni tree extract, and melon extract in amounts described above. The balance of the composition includes known cosmetic and topical formulation ingredients that are well-known to those of skill in the art and can include one or more of the ingredients described in U.S. Pat. No. 6,184,247 and in U.S. Pat. No. 6,579,516, the entire contents of which are incorporated herein by reference.

As an example only, certain cosmetic formulation ingredients may include, but are not limited to water; butylene glycol; castor oil; ethylene glycol monobutyl ether; diethylene glycol monoethyl ether; corn oil; dimethyl sulfoxide; ethylene glycol; isopropanol; soybean oil; glycerin; soluble collagen; zinc oxide; titanium oxide; or Kaolin. Other cosmetic formulation ingredients may include one or more humectants, including but not limited to: dibutyl phthalate; soluble collagen; sorbitol; or sodium 2-pyrrolidone-5-carboxylate. Other examples of humectants that may be used in practicing the present invention can be found in the CTFA (Cosmetic Toiletry and Fragrance Association) Cosmetic Ingredient Handbook, the relevant portions of which are incorporated herein by reference.

Acceptable cosmetic formulation ingredients may optionally include one or more emollients including but not limited to: butane-1,3-diol; cetyl palmitate; dimethylpolysiloxane; glyceryl monoricinoleate; glyceryl monostearate; isobutyl palmitate; isocetyl stearate; isopropyl palmitate; isopropyl stearate; butyl stearate; isopropyl laurate; hexyl laurate; decyl oleate; isopropyl myristate; lauryl lactate; octadecan-2-ol; caprylic triglyceride; capric triglyceride; polyethylene glycol; propane-1,2-diol; triethylene glycol; sesame oil; coconut oil; safflower oil; isoamyl laurate; nonoxynol-9; panthenol; hydrogenated vegetable oil; tocopheryl acetate; tocopheryl linoleate; propylene glycols; arachis oil; castor oil; isostearic acid; palmitic acid; isopropyl linoleate; lauryl lactate; myristyl lactate; decyl oleate; or myristyl myristate. Other examples of emollients that may be used in practicing the present invention can be found in the CTFA Cosmetic Ingredient Handbook, the relevant portions of which are incorporated herein by reference.

Cosmetic formulation ingredients may include penetration enhancers including but not limited to: pyrrolidones, for example 2-pyrrolidone; alcohols, such as ethanol; alkanols, such as decanol; glycols, such as propylene glycol, dipropylene glycol, butylene glycol; surfactants; or terpenes.

Other various known and conventional cosmetic adjuvants are contemplated so long as they do not detrimentally affect the desired protective to and repair of damage to nuclear DNA, mitochondrial DNA, or both, and/or protection or prevention of damage to such DNA from, for example, reactive oxygen species. For example, a composition of the present invention can further include one or more additives or other optional ingredients well known in the art, which can include but are not limited to vitamins, retinoids, and retinols (e.g., vitamin B.sub.3, vitamin A, etc.); pigments; fragrances; sunscreens and sunblocks; antioxidants and radical scavengers; organic hydroxy acids; exfoliants; skin conditioners; moisturizers; ceramides, pseudoceramides, phospholipids, sphingolipids, cholesterol, glucosamine, pharmaceutically acceptable penetrating agents (e.g., n-decylmethyl sulfoxide, lecithin organogels, tyrosine, lysine, etc.); antimicrobial agents; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, including but not limited to Aloe Vera, cornflower, witch hazel, elderflower, or cucumber; opacifiers; suspending agents; binders; preservatives; and combinations thereof. One example of a preservative that might be included is Phenonip® (Clariant, Charlotte, N.C.), an anti-microbial mixture of plant extracts including 2-phenoxyethanol and glycol ethers. Other suitable additives and/or adjuncts are described in U.S. Pat. No. 6,184,247, the entire contents of which are incorporated herein by reference.

The composition can include additional inactive ingredients, including, but not limited to surfactants, co-solvents, and excipients. Surfactants, such as hydrophilic and hydrophobic surfactants, can be included in the compositions. Particular surfactants can be used based on the on the overall composition and the intended delivery of the composition. Useful surfactants include polyethoxylated (PEG) fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, polysaccharide esters, polyethylene glycol alkyl phenols, polyoxyethylene-polyoxypropylene block copolymers, sorbitan fatty acid esters, lower alcohol fatty acid esters, ionic surfactants, and mixtures thereof.

Elaboration of the further myriad suitable ingredients is not necessary to understand the present invention. In certain embodiments, it is contemplated that the only plant extracts present in the composition are the candle bush extract, the noni tree extract, and the melon extract.

In a further alternative embodiment, the composition of the present invention consists essentially of an extract mixture that consists essentially of about 0.01% to about 1% of a candle bush extract, about 0.01% to about 1% of a noni tree extract, and about 0.05% to about 3% of a melon extract, with the balance comprising cosmetic ingredients.

In yet another embodiment, the composition of the present invention consists of an extract mixture that consists essentially of about 0.01% to about 1% of a candle bush extract, about 0.01% to about 1% of a noni tree extract, and about 0.05% to about 3% of a melon extract, with the balance comprising cosmetic ingredients. In this embodiment, it may be desirable to exclude other plant extracts.

Suitable forms of topical formulations include lotions, creams, butters, sticks, sprays, and other product forms that can be applied to the skin in a manner such that it functions as a leave-on product. Other suitable topical formulations include wash-off products although it is contemplated that such formulations may be less desirable than leave-on formulations. The active extracts (candle bush, noni tree, and melon) could be encapsulated or formulated as liposomes or in other forms to provide formulation stability or increased skin deposition or penetration.

The compositions of the present invention may be administered at least on a daily basis. Administration of the compositions of the invention may continue for any suitable period of time. It should be appreciated that the degree of repair of damage to nuclear DNA, mitochondrial DNA, or both, and/or degree of protection or prevention of damage to such DNA from, for example, reactive oxygen species, will vary directly with the total amount and frequency of composition used.

In one example, a composition of the present invention is administered at least once a day. In another example, a composition of the present invention may be administered twice daily. In a further example, a composition of the present invention may be administered three to five times daily. In another example, there is no limit on the amount of a composition of the present invention that might be administered daily. For best effect, compositions of the present invention are administered on at least a daily basis for at least a week to several weeks. Compositions of the present invention also may be administered on at least a daily basis for several weeks to a month to several months to a year to years. It should be appreciated that there is no limit on how frequently or how long the composition of the present invention is administered.

It is intended that the foregoing detailed description be regarded as illustrative rather than limiting. The present invention is further illustrated by the following experimental investigations and examples, which should not be construed as limiting. The contents of all references, patents and published applications cited throughout this patent are hereby incorporated by reference herein.

Example

In this example, cells are challenged with tertiary butyl peroxide (a ROS generator) in presence or absence of each of the candle bush extract, the noni tree extract, the melon extract, or the combination of all three extracts. The change in gene expression between the extract-treated cells and the untreated cells is measured.

Specifically, Human Fibroblast cells HS27 cell line were treated 0.3% DN-AGE LS 9653, 0.1% CITROFOLINE, 0.5% EXTRAMEL C, or the combination of all three (i.e., 0.3% DN-AGE LS 9653, 0.1% CITROFOLINE, 0.5% EXTRAMEL C) for 24 hrs. Subsequent to the treatment, the cells were lysed and the total RNA isolated. The isolated cellular RNA was used first to synthesize double strand cDNA and then biotin labeled amplified RNA (aRNA). The process from cDNA to aRNA synthesis was done using the Bioarray kit from Enzo Life Sciences. The synthesized aRNA was then used to hybridize Affymetrix human genomic gene chip, and gene profile and expression quantitated. The microarray hybridization was carried out in the Michigan State University microarray facility.

FIG. 1 shows the results and it can be see that the combination of the candle bush extract, noni tree extract, and melon extract, synergistically up regulated each of the SIRT1, Gadd45B, and SOD2 genes.

The above description is intended to illustrate the invention with the understanding that various alterations and changes can be made without departing from the spirit and broader aspects of the invention as defined in the claims.

The invention claimed is:

1. A composition comprising a candle bush extract, a noni leaf extract, and a melon extract in amounts effective to up regulate each SIRT1, Gadd45b, and SOD2; wherein the candle bush extract is present in an amount within the range between about 0.01% to about 1%, the noni leaf extract is present in an amount within the range between about 0.01% to about 1%, and the melon extract is present in an amount within the range between about 0.05% to about 3%.

2. The composition of claim 1 wherein the candle bush extract is present in an amount within the range between about 0.01% to about 1%.

3. The composition of claim 1 wherein the noni leaf extract is present in an amount within the range between about 0.01% to about 1%.

4. The composition of claim 1 wherein the melon extract is present in an amount within the range between about 0.05% to about 3%.

5. A topical cosmetic or dermatological composition comprising an extract mixture that comprises from about 0.01% to about 1% of a candle bush extract, from about 0.01% to about 1% of a noni leaf extract, and from about 0.05% to about 3% of a melon extract, and the balance comprising cosmetic ingredients.

6. A method of protecting or repairing oxidative damage comprising topically administering to a subject in need thereof a composition comprising a candle bush extract, a noni leaf extract, and a melon extract in amounts effective to up regulate each SIRT1, Gadd45b, and SOD2; wherein the candle bush extract is present in an amount within the range between about 0.01% to about 1%, the noni leaf extract is present in an amount within the range between about 0.01% to about 1%, and the melon extract is present in an amount within the range between about 0.05% to about 3%.

7. The method of claim 6 wherein the composition contains each of candle bush extract, noni leaf extract, and melon extract.

8. The method of claim 7 wherein the candle bush extract is present in an amount within the range between about 0.01% to about 1%.

9. The method of claim 7 wherein the noni leaf extract is present in an amount within the range between about 0.01% to about 1%.

10. The method of claim 7 wherein the melon extract is present in an amount within the range between about 0.05% to about 3%.

* * * * *